United States Patent
Raffy

(10) Patent No.: US 8,275,186 B2
(45) Date of Patent: Sep. 25, 2012

(54) METHOD AND APPARATUS FOR SETTING A DETECTION THRESHOLD IN PROCESSING MEDICAL IMAGES

(75) Inventor: Philippe Raffy, Sunnyvale, CA (US)

(73) Assignee: Hologic, Inc., Bedford, MA (US)

( * ) Notice: Subject to any disclaimer, the term of this patent is extended or adjusted under 35 U.S.C. 154(b) by 792 days.

(21) Appl. No.: 11/344,838

(22) Filed: Jan. 31, 2006

(65) Prior Publication Data

US 2007/0177782 A1 Aug. 2, 2007

(51) Int. Cl.
*G06K 9/00* (2006.01)
(52) U.S. Cl. ...................................... 382/129
(58) Field of Classification Search .................. 382/132
See application file for complete search history.

(56) References Cited

U.S. PATENT DOCUMENTS

| | | | |
|---|---|---|---|
| 7,809,175 B2 * | 10/2010 | Roehrig et al. | 382/128 |
| 2002/0144697 A1 * | 10/2002 | Betz | 128/920 |
| 2003/0161513 A1 | 8/2003 | Drukker | |
| 2004/0068187 A1 * | 4/2004 | Krause et al. | 600/443 |
| 2004/0120561 A1 * | 6/2004 | Goto | 382/128 |
| 2004/0252870 A1 | 12/2004 | Reeves et al. | |
| 2005/0036668 A1 | 2/2005 | McLennan et al. | |
| 2005/0207630 A1 * | 9/2005 | Chan et al. | 382/131 |
| 2006/0094954 A1 * | 5/2006 | Fan et al. | 600/425 |

* cited by examiner

*Primary Examiner* — Bhavesh Mehta
*Assistant Examiner* — Nirav G Patel

(57) ABSTRACT

An intuitive user interface is provided that allows for selection of an abnormality level in features in a medical image on the basis of graphical depictions of the abnormalities themselves. In one embodiment, the user interface displays realistic images of actual abnormalities in a series ranging from least severe to most severe and the medical practitioner selects the abnormality level by mouse-clicking on one of the images. The user interface then displays an annotated map of suspected abnormalities with annotations only on those suspected abnormalities that are at least as severe as the selected abnormality. In alternative embodiments, the user interface displays stylized images of the abnormalities plotted by the display using mathematical functions. In yet another alternative, the images are hand-drawn images.

14 Claims, 6 Drawing Sheets

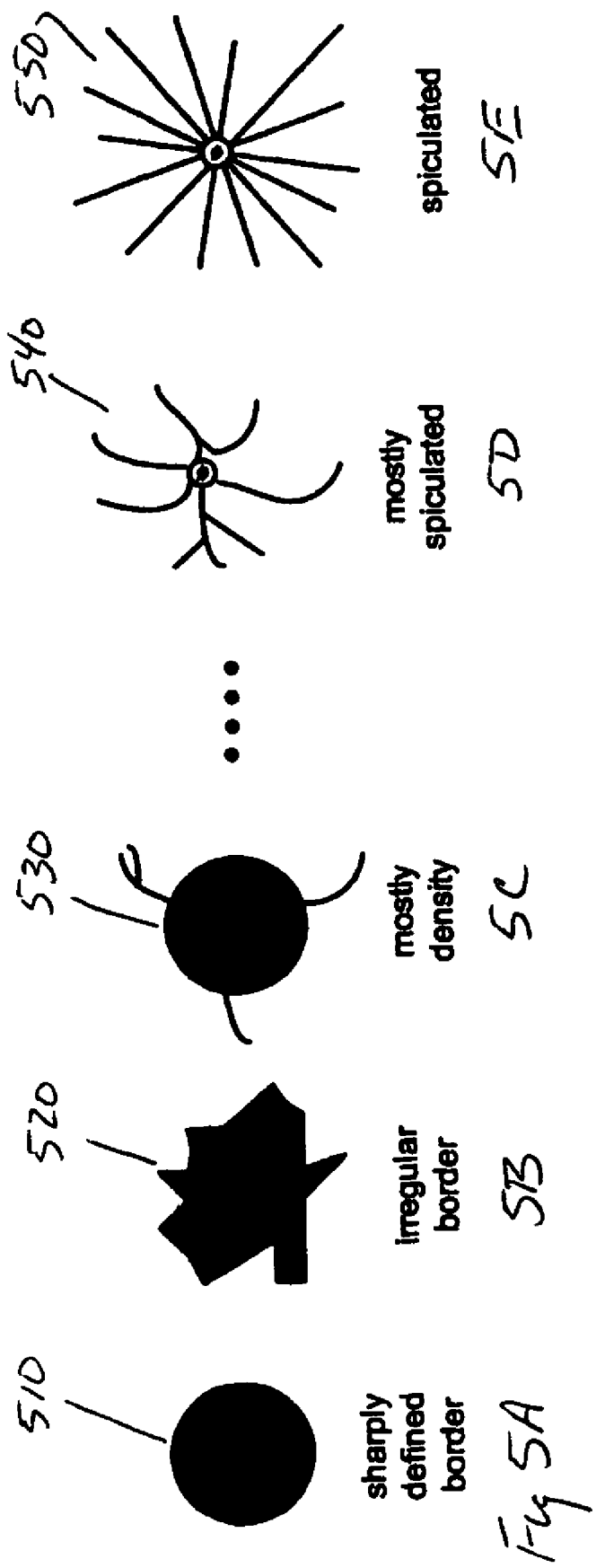

METHOD AND APPARATUS FOR SETTING A DETECTION THRESHOLD IN PROCESSING MEDICAL IMAGES

FIELD OF THE INVENTION

The invention disclosed herein relates to a method and apparatus for setting the detection threshold used for processing medical images.

BACKGROUND OF THE INVENTION

Over the last several years, computer aided detection systems have been developed that provide a "second reading" of a medical image such as a mammogram or a chest x-ray. Such systems take a mammogram or x-ray in digital form, process it to locate abnormalities, rank the abnormalities by a scoring algorithm and then display their results in the form of an annotated map that shows the locations of the suspected abnormalities and some measure of their ranking.

The ranking is typically a confidence level that the suspected abnormality is indeed truly an abnormality or a true positive. Alternatively, the ranking could be an estimate of the severity of the suspected abnormality. The ranking can be expressed in numerous ways. For example, it can be expressed numerically alongside a marker indicating the location of the suspected abnormality, or it can be expressed using different size markers for different probability or confidence levels, or different colors, or different shades of the same color. The use of such markers is described, for example, in S. P. Wang's U.S. Pat. No. 6,266,435 for "Computer-Aided Diagnosis Method and System" which is incorporated herein by reference. Examples of commercial use of such markers are found in the assignee's Mammochecker® mammography system and Imagechecker® MSCT system.

As described in the '435 patent, some of the suspected abnormalities will turn out to be of no concern. In other words, they are false positives. Indeed, in any detection system, there is a trade off between sensitivity, or the fraction of true positives detected, and specificity or the fraction of false positives detected. This sensitivity/specificity trade off is often depicted in the detection system's receiver operating characteristic (ROC) curve such as that shown in FIG. 1. The ROC curve is a plot 100 of the fraction of true positives detected (TPF) as measured on the ordinate or y axis versus the fraction of false positives detected (FPF) as measured on the abscissa or x axis. As the fraction of true positives detected (or sensitivity) increases, so does the fraction of false positives detected, thereby decreasing the specificity.

In the medical arts, the trade-off between sensitivity and specificity that is represented by the ROC curve is always a concern. If the detection system is not sensitive enough, it may report too few true positives (i.e., more false negatives) which typically represent missed opportunities to detect some sort of problem that may well be life-threatening. On the other hand, if the detection system is not specific enough, it may report too many false positives which typically will result in the performance of additional medical procedures to establish the true nature of the false positive and, in many cases, considerable emotional stress on the part of the patient. Faced with this trade-off, the medical practitioner is usually forced to set the threshold of his/her detection system by trial-and-error at some value that assures the detection of significant numbers of true positives at the cost of some false positives.

This problem is especially acute in the computer-aided detection (CAD) of lung modules in computer tomography (CT) images. Because large numbers of false positives are present in many CT lung images, it is desirable to permit the medical practitioner to vary the detection threshold. Usually, this is done by entering into the computer system a numerical value. The computer system will then report or mark those inputs that have a score that is in excess of the threshold and will ignore all other events. The number of false positives, however, will vary from one lung image to another and the need to suppress false positives will vary accordingly. Thus, the threshold value required to suppress excess false positives will also vary. In addition, the numerical ranges used in scoring the abnormalities are based on arbitrary scales and will vary from detection system to detection system. The result is that the medical practitioner is often forced into some trial and error process for setting the threshold or is required to consult some other source to determine a suitable threshold.

SUMMARY OF THE PRESENT INVENTION

In accordance with the present invention, a more intuitive user interface is provided which allows for selection of the abnormality level on the basis of graphical depictions of the abnormalities themselves. In particular, in one embodiment the user interface displays realistic images of actual abnormalities in a series ranging from least severe to most severe and the medical practitioner can select the abnormality level by mouse-clicking on one of the images. The user interface will then display the annotated map of suspected abnormalities with annotations only on those suspected abnormalities that are at least as severe as the selected abnormality.

In alternative embodiments, the user interface displays stylized images of the abnormalities plotted by the display using mathematical functions. In yet another alternative, the images are hand-drawn images.

BRIEF DESCRIPTION OF THE DRAWINGS

These and other objects, features and advantages will be more readily apparent from the following Detailed Description in which:

FIGS. 5A-5E are representations of mammographic lesions that may be used in the practice of the invention.

DETAILED DESCRIPTION

Figure 1:
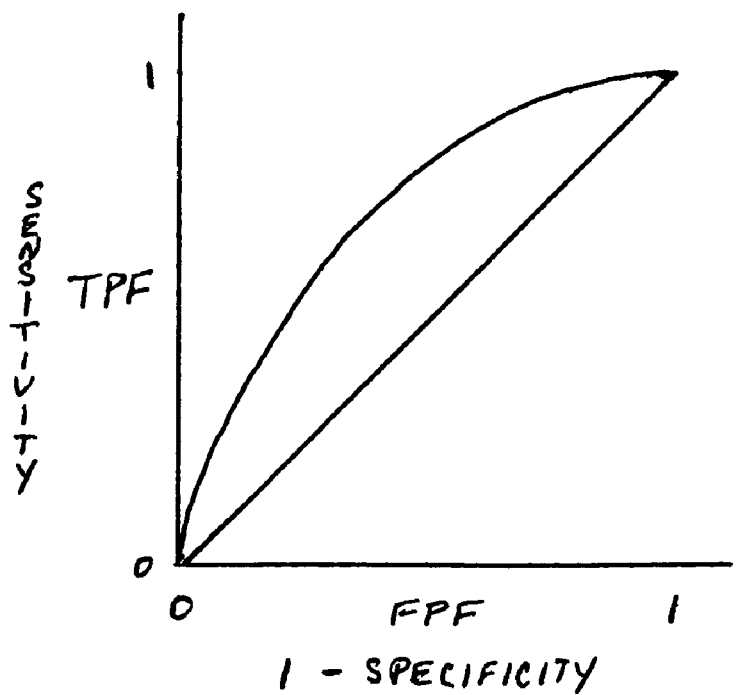
FIG. 1 depicts a receiver operating characteristic (ROC) curve for a detection system.
Figure 2:
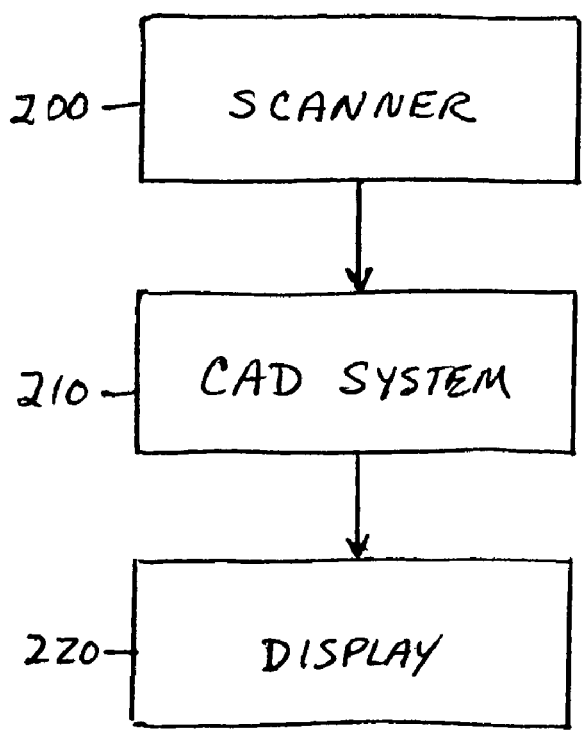
FIG. 2 depicts a detection system used in the practice of the invention.

FIG. 2 is a block diagram of illustrative apparatus used in the practice of the invention. The apparatus comprises a multi-slice computer tomography (MSCT) scanner 200, a computer-aided-detection (CAD) system 210 and a display 220. MSCT scanners are commercially available and are sold by companies such as General Electric and Siemens. The detection system and display can be a personal computer or a work station operating under control of a suitable computer program. The scanners produce a series of digital images that are x-ray images of a series of slices through the patient's body. The digital images are then processed by the CAD system and displayed on display 220.

The processing that is performed includes the processing that creates a visual image from the x-ray data obtained by the scanner. Advantageously, the processing may also include processing that combines the two-dimensional image data on each slice to form a perspective view of a three-dimensional anatomical structure. In addition, the processing may also include analysis of the digital images to detect features that may be of interest to a medical practitioner, e.g., features indicative of cancer and the like. One such prior art system is the assignee's ImageChecker® CT system. Certain details of this system are described in U.S. Pat. No. 6,925,200 which is incorporated herein by reference.

As indicated above, in prior art detection systems the medical practitioner sets the threshold for marking abnormalities in the CT lung images by entering a numerical value at the computer keyboard. The CAD system will then mark as abnormal only those features in the images that have a score that is greater than the threshold.

In the present invention, there is no need to enter a numerical value. Rather, a set of images are displayed on display 220 representative of the features that might be observed in a CT lung image. The images are displayed in order ranging from least severe to most severe and they are related by the CAD system to specific numerical scores. As a result, the medical practitioner can set a threshold visually by looking at the image features that concern him and then clicking on one of the images. The CAD system records which image was clicked and obtains the numerical score associated with that image. It then marks as abnormal only those features in the image that have a score that is greater than the numerical score and displays those features with the appropriate markings.

Figure 3:
FIGS. 3A-3O are images of typical lung nodule abnormalities.
Figure 3:
Figure 3:
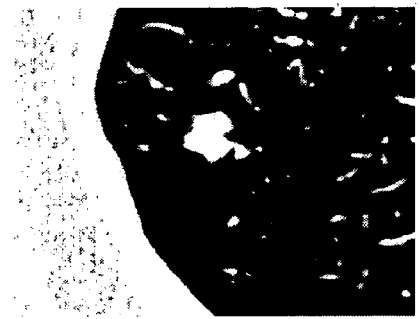
Figure 3:
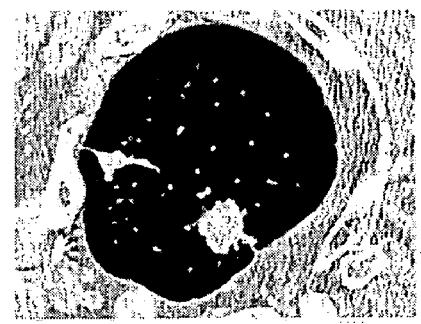
Figure 3:
Figure 3:
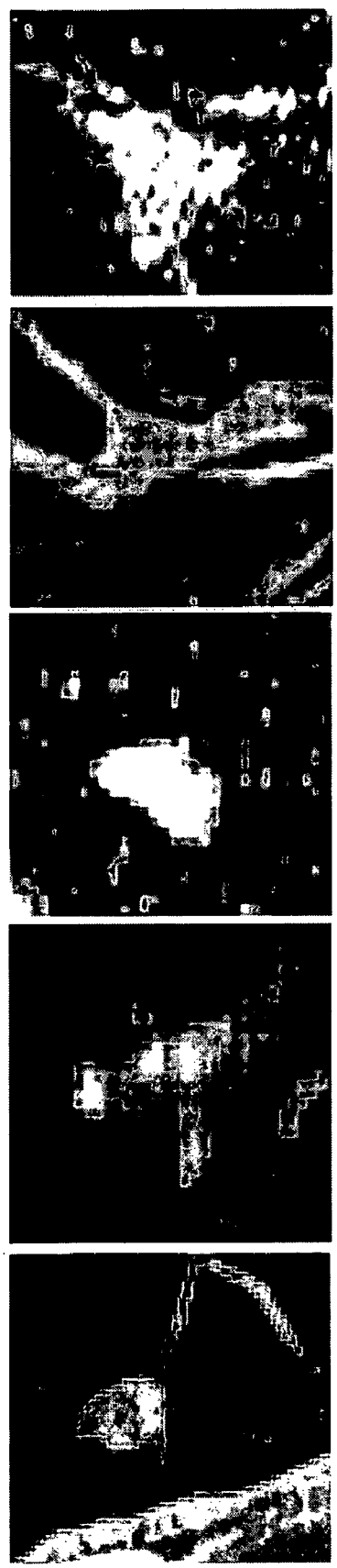
Figure 3:
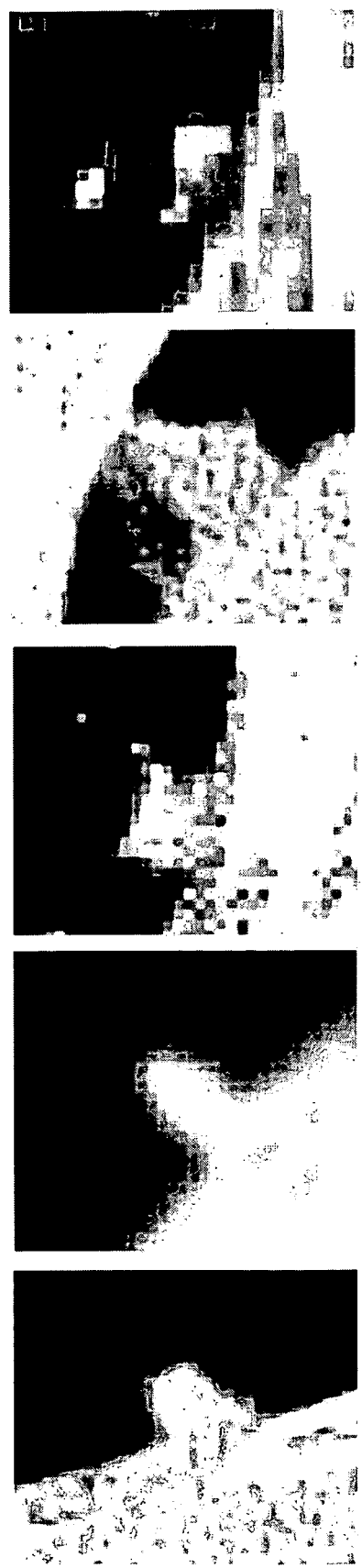
Figure 4:
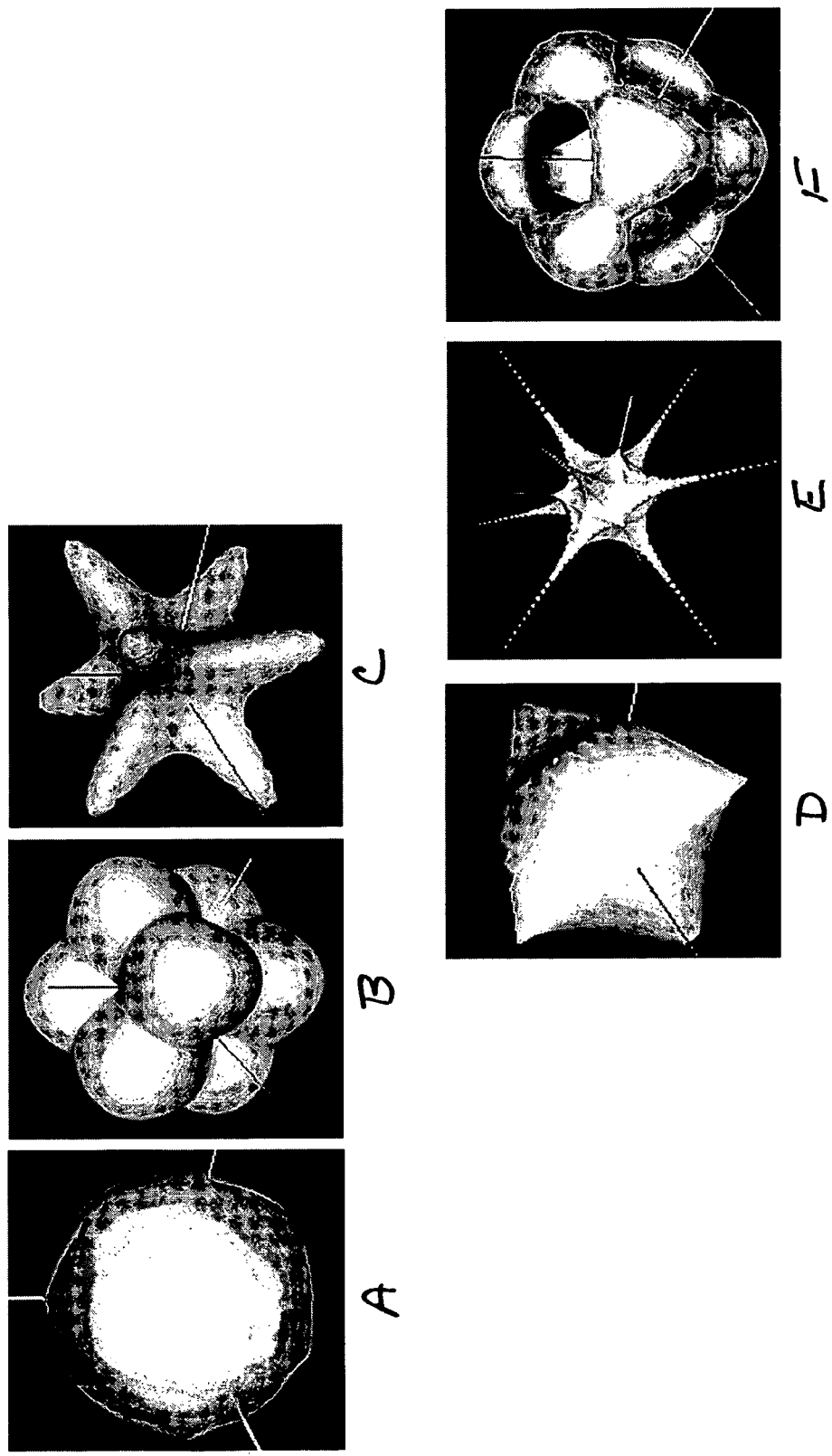
FIGS. 4A-4F are images of alternative nodule representations that may be used in the practice of the invention.

In one embodiment of the invention, the images displayed on display 220 are realistic images of actual abnormalities in a server ranging from least severe to most severe. Three sets of such images of lung nodule abnormalities are shown in FIGS. 3A-3O. FIGS. 3A-3E show nodules of different shapes. FIG. 3A depicts a round nodule 310; FIG. 3B depicts an elliptical nodule 320; FIG. 3C depicts a lobular nodule 330; FIG. 3D depicts a spicular nodule 340; and FIG. 3E depicts an excavated nodule 350. FIGS. 3F-3J show isolated nodules within the parenchyma; and FIGS. 3K-3O show plural nodules. Each of FIGS. 3A-3O is associated by the CAD system with a numerical score within the scoring range of the algorithm that is used to score the features of a CT lung image; and the scores decrease from left to right. For example, the isolated nodule shown in FIG. 3F has a score of 0.006 False Positives per case (FP/case) and the other isolated nodules have increasingly lower scores to a score of 9 FP/case for the nodule shown in FIG. 3J. Similarly, the pleural nodule shown in FIG. 3K has a score of 0.01 FP/case and the other pleural nodules have increasingly lower scores to a score of 6.4 FP/case for the nodule of FIG. 3O. The medical practitioner can set the threshold to be used in the scoring algorithm by moving a mouse or other computer input device to the image that corresponds most closely to the least severe abnormality that he wants to be marked by the CAD system and clicking on that image. The CAD system then retrieves the score associated with that image and uses it as the threshold for determining which features to mark in the CT lung image.

Alternatively, the images that are used could be synthetic images such as those shown in FIGS. 4A-4F instead of images of actual abnormalities. Again, the CAD system associates a numerical score with each image and the medical practitioner selects one image by clicking on it with an appropriate input device. The score associated with the image is then used as the threshold in the scoring algorithm so that only abnormalities having a higher score are marked by the CAD system.

While the invention is particularly useful in the setting of thresholds for CT lung images, it may also be practiced in setting other thresholds. For example, it may be used in setting the threshold for a CAD system used to mark abnormalities on mammograms. Again, the images that are used may be images of actual abnormalities or synthetic images representative of such abnormalities. Alternatively, they may be hand drawn sketches of typical abnormalities. One such set of sketches for detecting abnormalities in mammograms is shown in FIGS. 5A-5E. FIG. 5A depicts a lesion 510 with a sharply defined border; FIG. 5B depicts a lesion 520 with an irregular border; FIG. 5C depicts a lesion 530 that has some speculations but is mostly density; FIG. 5D depicts a lesion 540 that is mostly spiculated; and FIG. 5E depicts a lesion 550 that is fully spiculated. Again, the CAD system associates a numerical score with each image and the medical practitioner selects one image by clicking on it with an appropriate input device. The score associated with the image is then used as the threshold in the scoring algorithm so that only abnormalities having a higher score are marked by the CAD system.

What is claimed is:

1. A method for determining a threshold for display of regions of interest, the threshold used by a computer aided detection device for analysis of medical images and the method operating on a computer having a display for displaying the medical images, the method comprising:
    displaying a plurality of images on the display, each of the images having a different
    abnormality selected from a range of different abnormalities that may be observed in an anatomical image on the display,
    receiving, from a user interface, a selection of one of the images and an associated selected abnormality, and
    displaying, in response to said selected image and associated selected abnormality, an anatomical image in which abnormalities less severe than the selected abnormality are not annotated.

2. The method of claim 1 wherein the abnormalities in the anatomical image are scored to produce a set of scores, said method further comprising:
    establishing a threshold having a value that depends on the abnormality of the selected image; and
    comparing each score of the set of scores with the threshold to determine which abnormalities to annotate.

3. The method of claim 1 wherein the images are images of actual abnormalities.

4. The method of claim 1 wherein the images are images of actual abnormalities in lung nodules.

5. The method of claim 1 wherein the images are representative of abnormalities.

6. The method of claim 5 wherein the images are generated mathematically.

7. The method of claim 5 wherein the images are hand-drawn.

8. In a system for displaying medical images in which certain abnormalities are annotated, a method comprising:
    displaying a plurality of images, each image of the plurality having an abnormality selected from a range of different abnormalities that may be observed in an anatomical image,
    receiving, from a user interface, a selection of one of the images having an associated selected abnormality, and
    displaying, in response to the selection of the one of the images having the associated selected abnormality, an anatomical image in which abnormalities less severe than the selected abnormality of the selected image are not annotated.

9. The method of claim 8 further comprising:
    scoring the abnormalities in the anatomical image to produce a set of scores;

establishing a threshold having a value that depends on which image is selected; and comparing each score of the set of scores with the threshold to determine which abnormalities to annotate.

10. The method of claim 8 wherein the images are images of actual abnormalities.

11. The method of claim 8 wherein the images are images of actual abnormalities in lung nodules.

12. The method of claim 8 wherein the images are representative of abnormalities.

13. The method of claim 12 wherein the images are generated mathematically.

14. The method of claim 12 wherein the images are hand-drawn.

\* \* \* \* \*